(12) United States Patent
Zhang (10) Patent No.: US 9,279,786 B2
(45) Date of Patent: Mar. 8, 2016

(54) METHOD OF AND AN APPARATUS CONDUCTING CALIBRATION FOR PHASED-ARRAY SHEAR WAVE CHANNELS INSPECTING SQUARE BARS

(75) Inventor: Jinchi Zhang, Quebec (CA)

(73) Assignee: OLYMPUS NDT, Waltham, MA (US)

(*) Notice: Subject to any disclaimer, the term of this patent is extended or adjusted under 35 U.S.C. 154(b) by 544 days.

(21) Appl. No.: 13/591,893

(22) Filed: Aug. 22, 2012

(65) Prior Publication Data

US 2013/0047697 A1    Feb. 28, 2013

Related U.S. Application Data

(60) Provisional application No. 61/526,552, filed on Aug. 23, 2011.

(51) Int. Cl.
| | |
|---|---|
| *G01N 29/00* | (2006.01) |
| *G01N 29/26* | (2006.01) |
| *G01N 29/04* | (2006.01) |
| *G01N 29/27* | (2006.01) |

(52) U.S. Cl.
CPC ............ *G01N 29/262* (2013.01); *G01N 29/043* (2013.01); *G01N 29/27* (2013.01); *G01N 2291/106* (2013.01); *G01N 2291/2626* (2013.01); *G01N 2291/2634* (2013.01)

(58) Field of Classification Search
CPC ................................ B07C 5/00; H01L 21/67
USPC ................................................ 73/1.82, 1.86
See application file for complete search history.

(56) References Cited

U.S. PATENT DOCUMENTS

| | | | | |
|---|---|---|---|---|
| 6,415,644 | B1* | 7/2002 | Rockwood et al. | 73/1.86 |
| 8,746,069 | B2* | 6/2014 | Smythe | 73/598 |

OTHER PUBLICATIONS

"Advances in Phased Array Ultrasonic Technology Applications", 2007, chapter 7, pp. 315-414.*

* cited by examiner

*Primary Examiner* — Nashmiya Fayyaz
(74) *Attorney, Agent, or Firm* — Ostrolenk Faber LLP (57) ABSTRACT

Disclosed is a system and method suitable for calibrating a phased array system configured to inspect square bars. A square bar is provided with an array of parallel linear notches across the full range of the testing surface of the square bar for this calibrating purpose. The square bar is passed through the probe in probe's passive direction during the calibration. The phased array system is adjusted and calibrated so that the echo amplitude for each inspection channel of the phased array probe received from each notch is substantially equal. Then a known flaw with a typically expected flaw's size and shape is created on the same testing surface so that the system's sensitivity is adjusted using the amplitude of the echo signal from the known flaw as a baseline.

16 Claims, 9 Drawing Sheets

METHOD OF AND AN APPARATUS CONDUCTING CALIBRATION FOR PHASED-ARRAY SHEAR WAVE CHANNELS INSPECTING SQUARE BARS

CROSS REFERENCE TO RELATED APPLICATION

This application claims the benefit and priority of U.S. Provisional patent application Ser. No. 61/526,552 filed Aug. 23, 2011 entitled A METHOD OF AND AN APPARATUS CONDUCTING CALIBRATION FOR PHASED-ARRAY SHEAR WAVE CHANNELS INSPECTING SQUARE BARS, the entire disclosure of which is incorporated herein by reference.

BACKGROUND OF THE DISCLOSURE

In an in-line ultrasonic phased-array system of inspection for round bars or square bars, shear waves (shear wave) are often used to inspect the zones on and under the bar surface (subsurface), called near wall zones. For round bar inspection, usually several circular PA probes are arranged concentrically around the bar being inspected; each PA probe fires respectively clock wise (CW) and counter-clock wise (CCW) shear wave beams in an angle to the bar surface, such as 40 degrees, to inspect the surface and subsurface zones. For square bar inspection, usually flat linear PA probes are arranged in parallel to and over each side of the bar; each PA probe fires respectively CW and CCW shear wave beams of about 40 deg into the corresponding surface (for example top surface) from water couplant and the sound beams transmit to the two adjacent surfaces (for example the right and left vertical surfaces).

Before any inspections, the sensitivities of the shear wave beams have to be calibrated with one or more artificial flaws, typically subsurface side-drilled-holes (SDH) or surface notches.

Description on round bar inline inspection can be found in section 5.10.2 in <<Introduction to phased array ultrasonic technology applications>> (ISBN 0-9735933-O-X) which describes generally round bar inspection.

The calibration is not difficult to achieve for round bars, because of the revolution symmetry and rotatable nature of round bars. In more details, when a near wall SDH or a surface notch in a round calibration bar rotates with the bar around the bar axis, all focal laws can detect the same flaw and then the detection sensitivities are obtained and compensated by the software of the inspection system.

To calibrate a square bar, the above calibration method cannot be applied because a square bar doesn't have revolution symmetry.

Existing approaches in square bar in-line inspection can be found in the figure 7-105 in <<Advances in phased array ultrasonic technology applications>> (ISBN 0-9735933-4-2) which roughly describes square bar surface inspection using SW waves, the content of which is herein incorporated by reference.

Patent research for shear wave channel calibration of square bar has been carried out, but nothing similar has been found.

Similarly to the calibration practice in ultrasonic inspection of square or rectangular parts, by translating the PA probe in beam plane, the sensitivities of a shear wave channel may be calibrated with subsurface SDHs or surface notches made in the surface to inspect. In more details, a series of flaws at different depths or sound paths are made in the surface to inspect and when the PA search unit moves in probe active plane the beams can perpendicularly cross the flaws, thus allowing the sensitivities being detected. However, in the practice of in-line inspection, this calibration method is not convenient to use because, i) to achieve the translation movement of the PA probes that are arranged equally around the square bar, the movement mechanism may become very complex, ii) such mechanism is prone to introducing PA probe positioning error through backlashes of movement.

SUMMARY OF THE INVENTION

The disclosed invention is related to a system and method suitable for calibrating a phased array system configured to inspect longitudinal square bars. A calibration longitudinal square bar is provided to have an array of parallel linear notches across the full range of the testing surface of the square bar. The square bar is passed through the probe in the probe's axial direction during the calibration. The phased array system is adjusted and calibrated so that the echo amplitude for each inspection beam of the phased array probe received from each notch is substantially equal.

In a preferred embodiment, a phased array non-destructive inspection system is configured to perform shear wave inspection on square bars, the system comprising: at least one phased probe having a plurality of apertures, with each aperture having at least one ultrasonic inspection element and the probe is applied with ultrasonic focal laws to form a linear scan channel which includes a plurality of ultrasonic beams, with each of the beams having echo signals including an echo amplitude, and each of the beams corresponds to one of the apertures; a longitudinal calibration square bar having four side walls as four test surfaces, at least one of which having an array of parallel linear notches indented across substantially full range of the testing surface, the longitudinal direction of the linear notches is largely in the same direction as the axial direction of the square bar, the square bar configured to be passed through the probe with its axial direction perpendicular to the probe's active direction during the inspection; wherein each inspection beam passes across at least one of the notches, and the inspection system is configured to conduct equilibration of the probe by adjusting each inspection element so that the echo amplitude for each beam corresponding to each notch is presented as substantially equal. The calibration square bar preferably has substantially the same size and shape as those of the testing target square bars, and the notches are slighted tilted such that the longitudinal direction of the notches and the axial direction of the bar form a tilted angle α, so that the relationship among notch pitch d, notch length L and the tilted angle α is defined as:

$$d < L \sin \alpha$$

The titled angle α can be in a range of 3 to 5 degrees.

The inspection system further preferably comprises a software or firmware module which can be executed to perform the equilibration of the probe by automatically adjusting the gain of each element so that the echo amplitude for each beam corresponding to each notch is presented as substantially equal, and the calibration square bar is further configured with a known standard reflector on or near the testing surface, the known reflector having a size and a shape of typical flaws expected from a typical testing target, wherein the inspection system's sensitivity is calibrated by adjusting a baseline amplitude received from the echo signal from the reflector to a predetermined operation level. The baseline amplitude is preferably obtained from one of the beams having the maximum amplitude representing echo from the standard reflector.

The invention includes a method of conducting calibration of a phased array non-destructive inspection system and a probe, the system is configured to perform shear wave inspection on square bars, and the probe having a plurality of apertures, with each aperture having at least one ultrasonic inspection element and the probe is applied with ultrasonic focal laws to form a linear scan channel which include a plurality of ultrasonic beams, with each of the beams having echo signals including an echo amplitude, and each of the beams is corresponding to one of the apertures, the method comprising: providing a longitudinal calibration square bar having four side walls as four test surfaces, at least one of which has an array of parallel linear notches indented across substantially full range of the testing surface, the longitudinal direction of the linear notches is largely in the same direction as the axial direction of the square bar, the square bar configured to be passed through the probe with its axial direction perpendicular to the probe's active direction during the inspection; operating the inspection system so that the beam passes across at least one of the notches; and conducting equilibration of the probe by adjusting each inspection element so that the echo amplitude for each beam corresponding to each notch is presented as substantially equal. Preferably, the calibration square bar has substantially the same size and shape as those of the testing target square bars, and the notches are slighted tilted such that the longitudinal direction of the notches and the axial direction of the bar form a tilted angle α, and providing the calibration square bar with a known standard reflector on or near the testing surface, the known reflector having a size and a shape of typical flaws expected from a typical testing target; and calibrating the sensitivity of the inspection system by adjusting a baseline amplitude received from the echo signal from the reflector to a predetermined operation level.

DETAILED DESCRIPTION OF THE PRESENT DISCLOSURE

Description of Basic Embodiment

The method of calibration of a PA system for square bar inspection includes two major steps, with the first step called equilibration calibration, as described below relative to FIGS. 1-3 and 7. The second step is called sensitivity calibration, described and shown in FIGS. 4a, 4b, 8 and 9.

Figure 1:
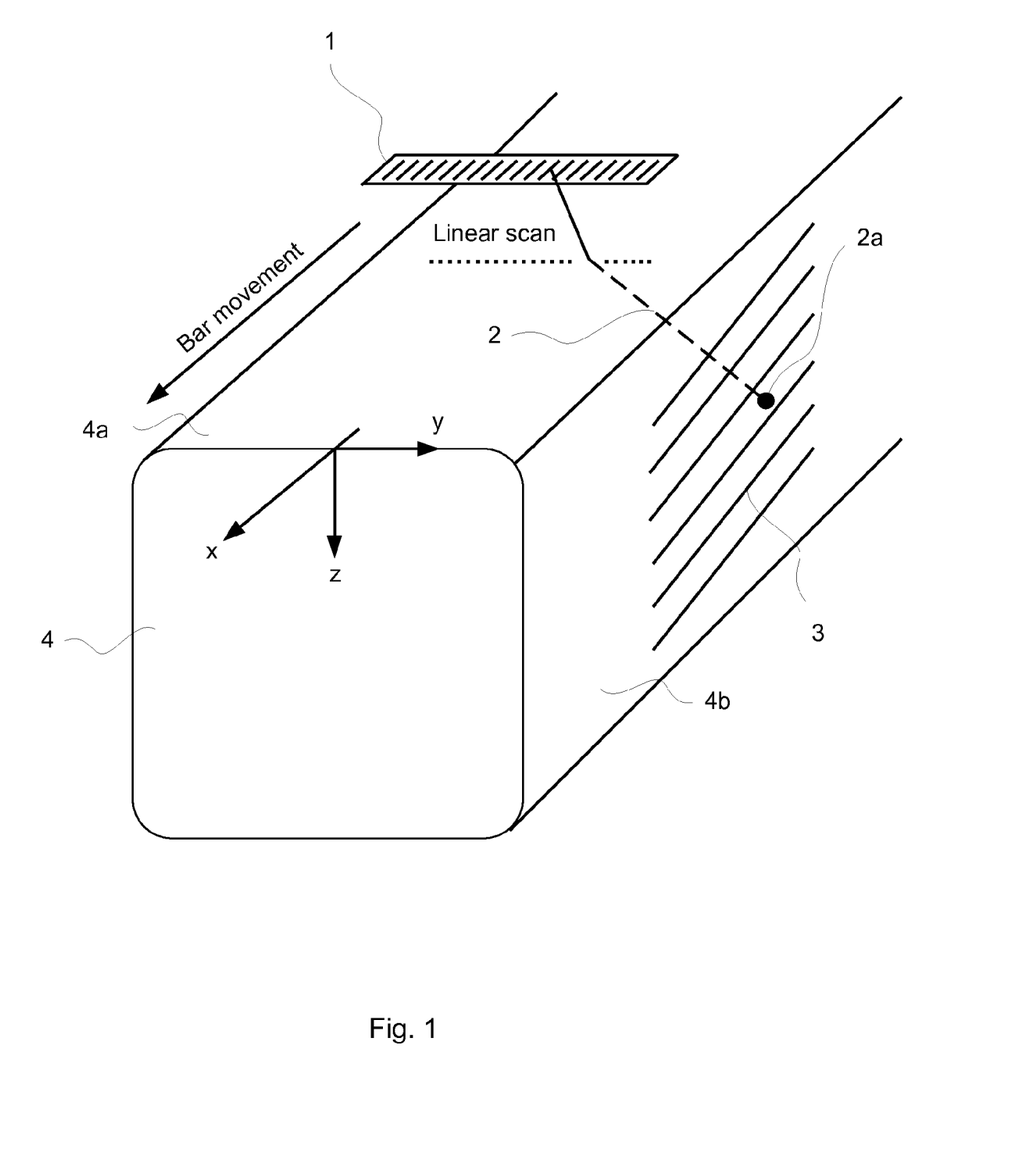
FIG. 1 is a perspective view of shear wave channel calibration for square bar inspection employing a calibration square bar applied with parallel notches on an inspection surface (wall) according to the presently disclosed embodiment.

Referring to FIG. 1, the first step of shear wave beam calibration, equilibration calibration, is set up with a calibration square bar 4 passing through a phased array probe 1 in its axial direction (x). Parallel, equal-depth notches 3 are applied across the width of an inspection surface, to a side wall 4b. It should be noted that the geometric characteristics of all notches 3, including the depth and the tilted angles, are machined to be the same and as uniform as possible.

Continuing with FIG. 1, probe 1 preferably has a plurality of apertures (not shown), and each aperture emits and receives response for at least one ultrasonic beam 2. An inspection or calibration channel is formed by a linear scan of a plurality of beams 2 either in clock wise or counter-clock wise fashion. The ultrasonic beam or the beams generated from a scan are also called focal laws.

As shown in FIG. 1, one of shear wave focal laws 2 detects a tilted notch when the end of the beam 2a passes through in bar axial direction x the notched zone 3. Note that the so-called square bar can have right angle corners or round corners. The shear wave beams 2 transmit from bar surface 4a to side wall 4b. Notches 3 on side wall 4b are preferably slightly tilted from the bar axial direction x. As bar 4 moves along the x axis, shear wave beams 2 scan the notch zone including notches 3 and detect the notches. The tilted notches are so arranged that every beam end 2a can always at least cross a portion of one or two notches as the bar moves in the x direction. By measuring the amplitude of echo of each shear wave beam 2 responded from each notch of the notch zone 3, the sensitivities of the shear wave beams can be compensated and then equilibrated with the help of the software of the inspection system.

Figure 2:
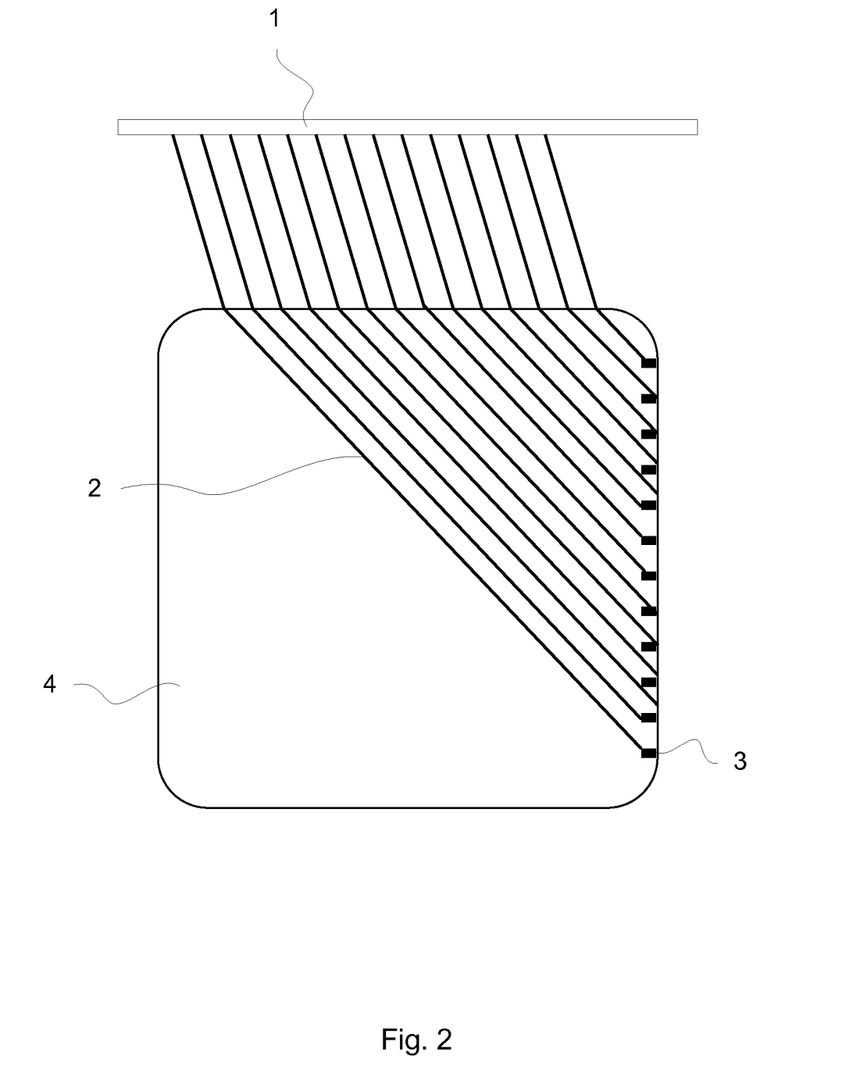
FIG. 2 is a cross-sectional view of shear wave channel calibration setup of FIG. 1, for one of the PA probes that does CW sear wave inspection.
Figure 3:
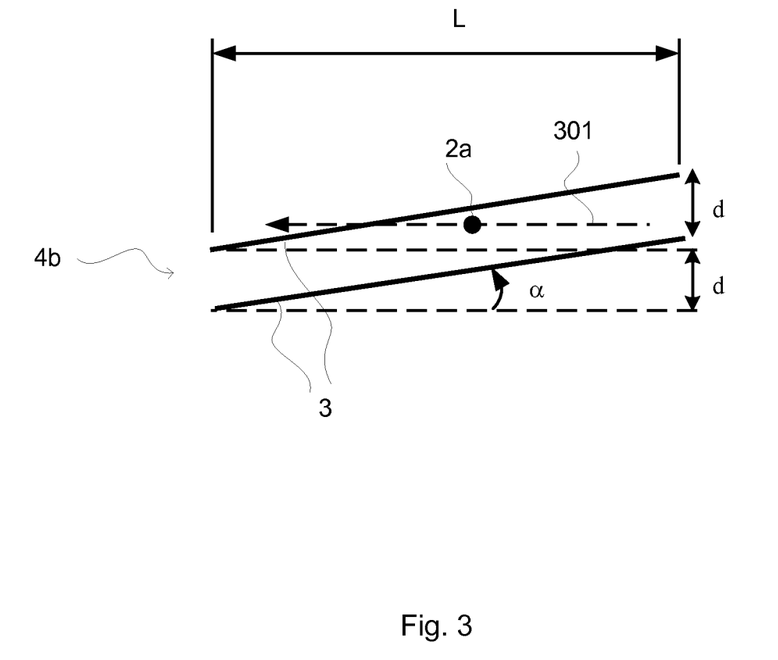
FIG. 3 is a diagram showing the geometric relation between notch tilted angle, notch length L and notch pitch d, wherein each beam end 2a that ends at the sidewall 4b crosses at least once notch 3 when the calibration bar 4 moves in bar axial direction and scanned by shear wave beam set 2.

In this step of equilibration calibration associated with FIGS. 1-3, the gain for each element is compensated so that the echo amplitudes received from each notch of notch zone 3 are equal.

Keeping the tilted notches as strong reflectors for shear wave beams can improve the signal uniformity when some minor non-homogeneity of material presents itself in the volume of the calibration bar. For this purpose, the tilted notch angle (α as shown in FIG. 3) is preferably limited to 3-5 degrees, and the into-wall depth of the tilted notches is uniform for each notch and is typically up to 1.5 to 2 mm.

Referring to FIG. 2, a sectional view corresponding to the projection view of FIG. 1 showing the shear wave beams 2 and the square bar 4 with a notched zone 3 is shown.

Reference is now made to FIG. 3, assisted by referring back to FIGS. 1 and 2, to describe geometric relations among tilted notch angle α, notch length L and notch pitch d. Two notches are representatively shown on wall 4b. Each beam end 2a moves or scans on side wall 4b, in the bar axial direction 301. The measurement of beam sensitivity requires that the beam end 2a should cross at least once a tilted notch as the bar moves in bar axial direction. To satisfy this condition, the parameters α, L and d must satisfy the following relation:

$$d < L \sin \alpha \qquad \text{Eq. 1}$$

The foregoing portion of this Detailed Description associated with in FIGS. 1 and 2 is for the purpose of seeking equilibration (equalizing) of focal laws of each beams exerted on each notch 3. Next, making reference to FIGS. 4a and 4b, the second step of calibration is done for the overall sensitivity of the share wave beams as a whole channel collectively. This step is called "Sensitivity Calibration".

Figure 4A:
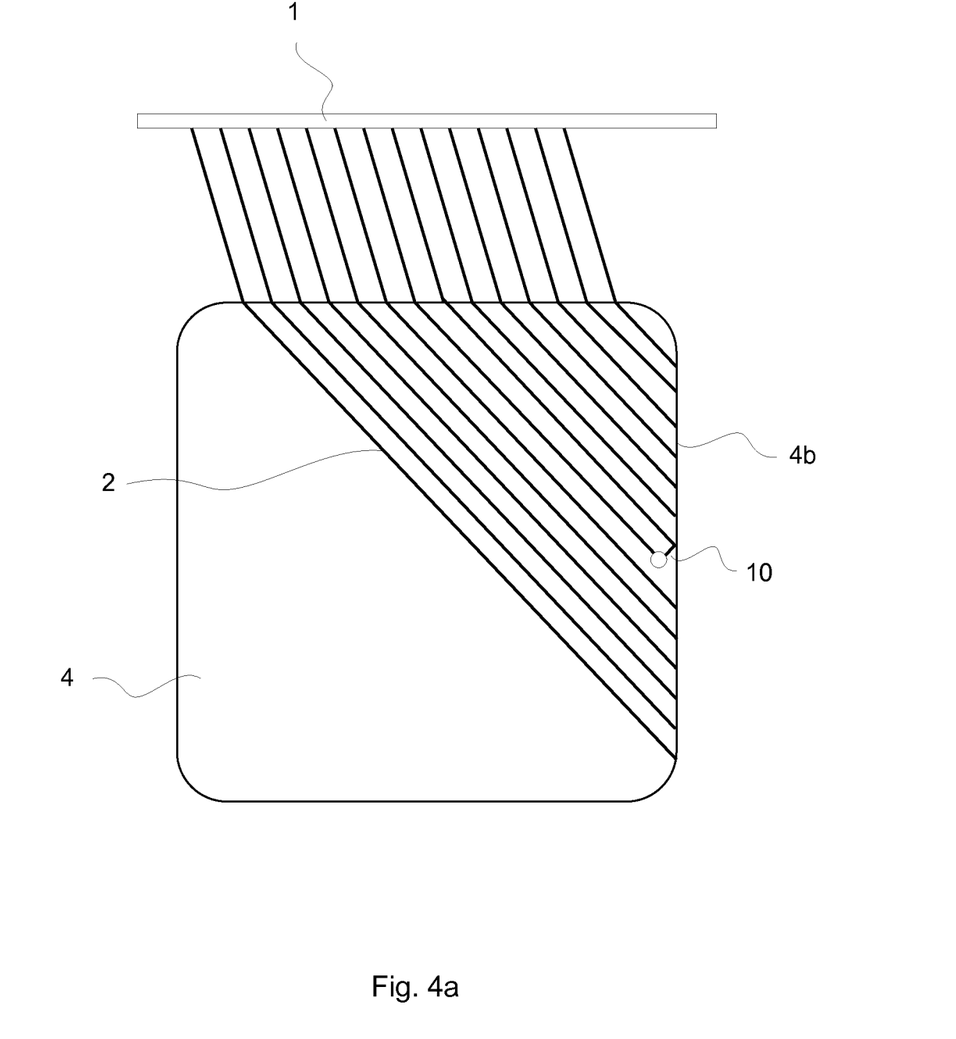
FIG. 4a shows the calibration steps according to the present disclosure for calibrating the shear wave channel sensitivity with a near wall side drill hole (herein after SDH) 10 that is made in parallel to bar axis.
Figure 4B:
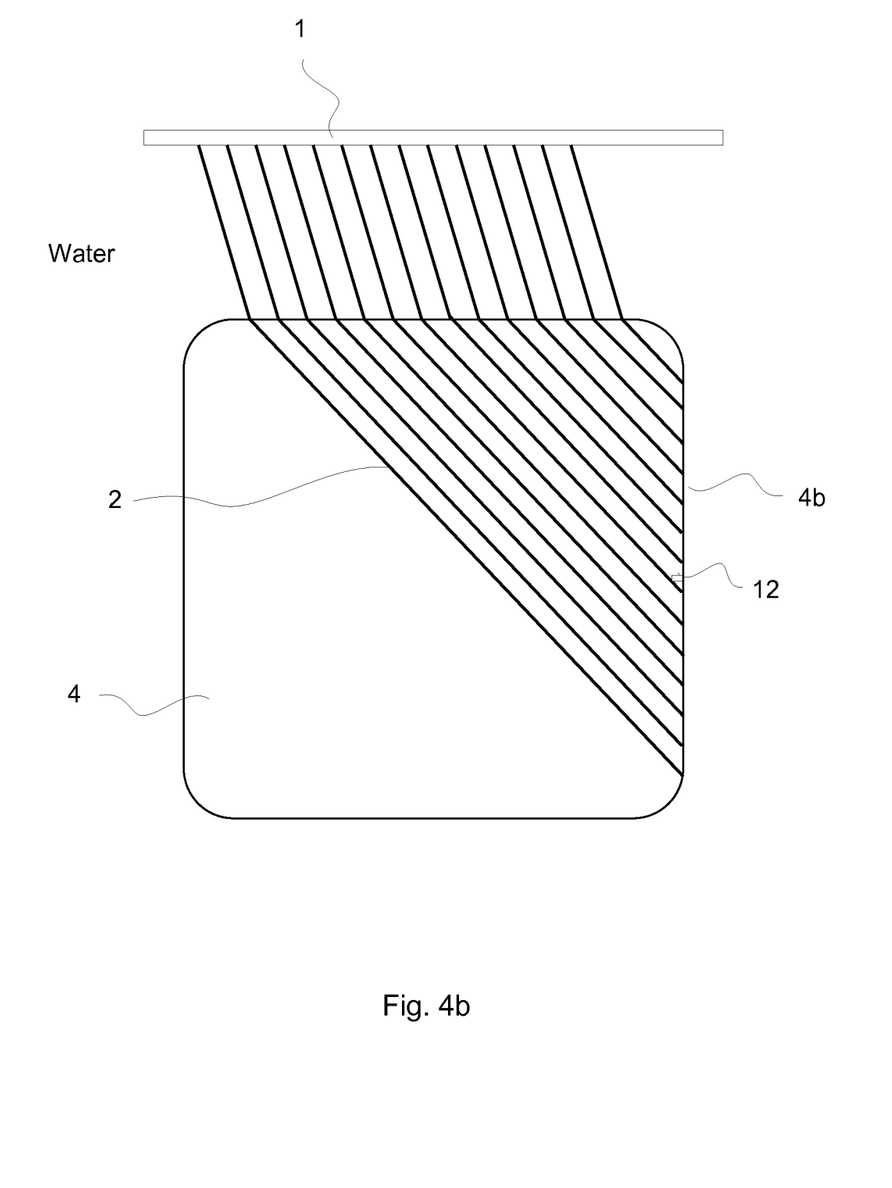
FIG. 4b shows calibration of the shear wave channel sensitivity with a surface notch that is made in parallel to bar axis. Here calibration of one of the beams 2 is sufficient.

Sensitivity calibration can be done by employing some known indications (defects) with known positions and known geometric characteristics. Known and often used indications, such as a side-drill-hole (herein after SDH) 10, and sensitivity standard notch 12 are exemplary usage for sensitivity calibration.

According to FIG. 4a, the presently disclosed embodiment includes employing a near wall SDH 10. The axial direction of SDH 10 is parallel to the axial direction of bar 4. Normally the SDH is a weaker reflector than the tilted notches. Sensitivity calibration is performed in the same way as existing practice for PA sensitivity calibration. The amplitude of echo signals associated with the known SDH 10 is used as a baseline. In principle, by adjusting the baseline of any one focal laws to the required amplitude level (e.g., to 80% Full Screen Height (FSH)), the sensitivities of other focal laws 2 are also adjusted at the same time since they are linked and equilibrated in the previous step described in FIG. 1 or FIG. 2. Calibration of one of the shear wave beams 2 is sufficient.

In reality, when detecting a subsurface SDH 10 with a shear wave beam 2 that has a certain beam width, the echo signal normally includes three major components, respectively corresponding to the following three sound paths: 1) a sound path that is a direct round trip to the SDH without interaction with the side wall 4b, 2) a sound path that goes through the SDH 10, and after being intercepted by the SDH 10 continues to go to the side wall 4b and finally returns to the beam aperture (note that the inverse sound path exists), and 3) a sound path that is a round trip to the SDH 10 via a reflection of the side wall 4b. These components are all within a very short range of time of flight since the SDH 10 is very near the wall. It is known to those skilled in the art that one gated beam detects only one component that has the maximum amplitude in the echo signal. It is possible that several adjacent beams detect different components at different amplitudes. As known to those skilled in the art, it is often the second sound path that presents the maximum amplitude. For the sake of simplicity, hereafter the beam that detects the SDH 10 with maximum amplitude is called "the beam corresponding to the SDH". Similarly to the known practice used in other existing sensitivity calibration technique, it is the sensitivity of the beam corresponding to the SDH to be applied to the other beams in sensitivity calibration.

Reference is now made to FIG. 4b, which describes an alternative second step of sensitivity calibration by using a standard notch 4. As shown in FIG. 4b, the overall sensitivity of the shear wave channel is determined with a surface standard notch that is parallel to the bar axial direction x. Normally standard notch 12 is shallower than tilted notches 3 on the side wall and therefore it is a weaker reflector. In most of existing phased array system, by adjusting the sensitivity of any one of focal laws to the required amplitude level (e.g., 80% full screen height), the sensitivities of other focal laws are also adjusted at the same time since they are commonly connected and equilibrated in the previous step described in FIG. 1 or FIG. 2.

Figure 5:
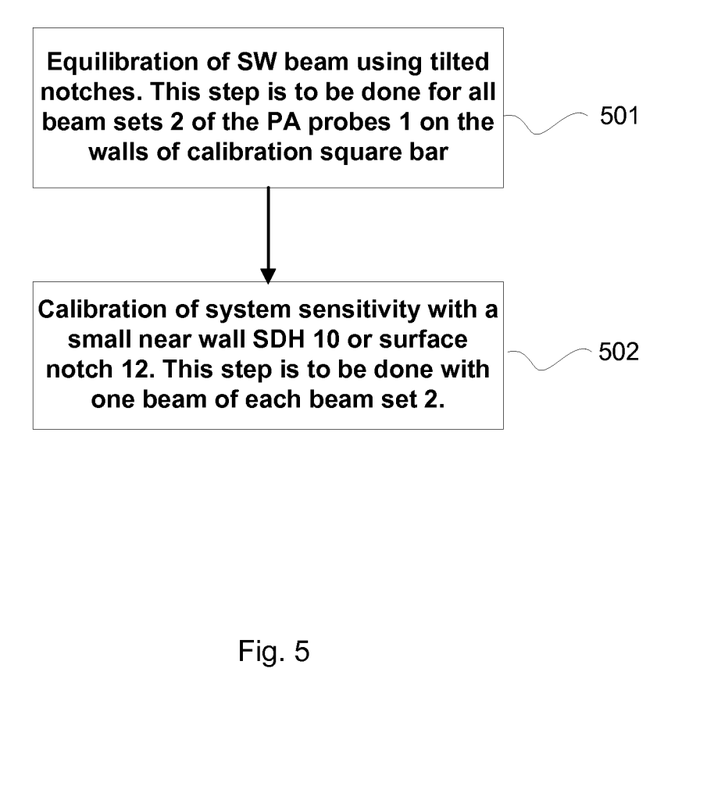
FIG. 5 is a block diagram showing calibration steps.
Figure 6A:
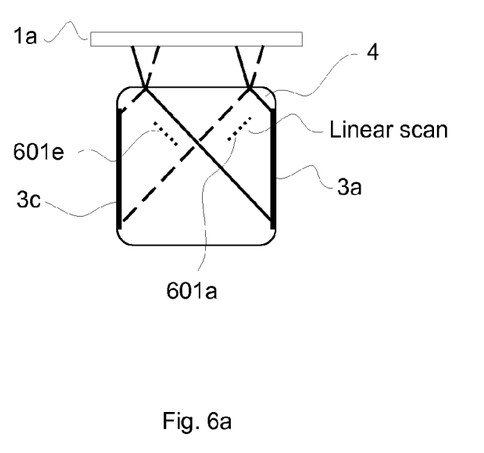
FIGS. 6a, 6b, 6c and 6d illustrate the equilibration step carried out for four walls of the square bar. Zones of titled notches 3a to 3d in a calibration bar 4 and the corresponding shear wave channels 701a to 701h are used associated with four probes.
Figure 6B:
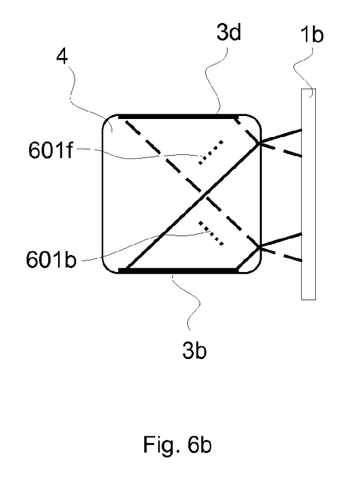
Figure 6C:
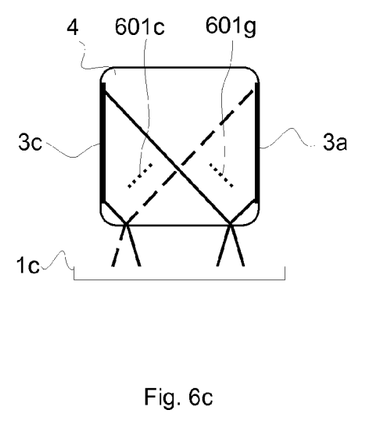
Figure 6D:
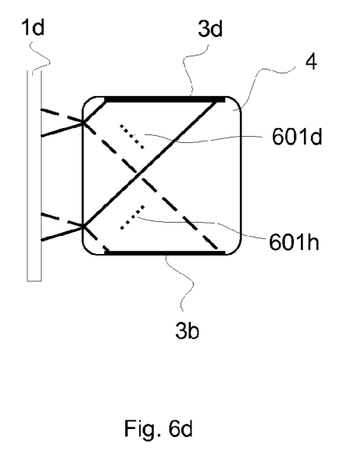
Figure 7A:
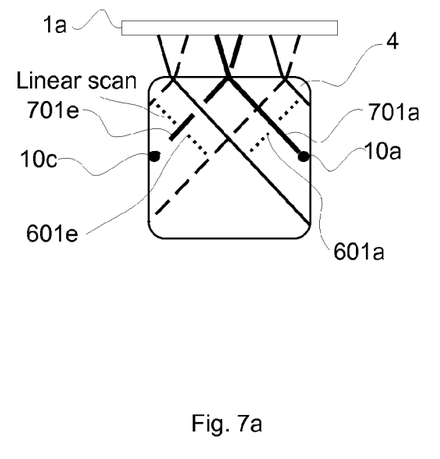
FIGS. 7a, 7b, 7c and 7d describe the overall sensitivity calibration step (step 2) carried out for four walls by using four subsurface SDHs 6a to 6d.
Figure 7B:
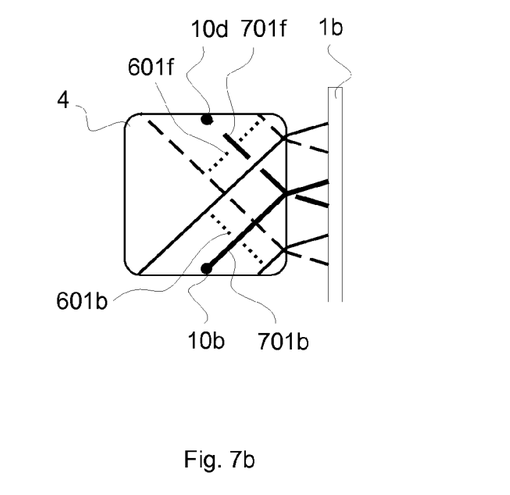
Figure 7C:
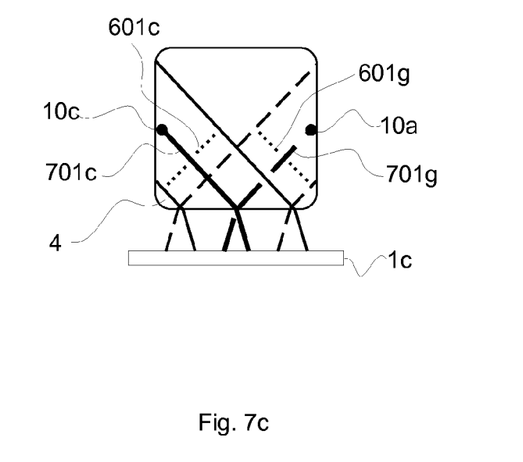
Figure 7D:
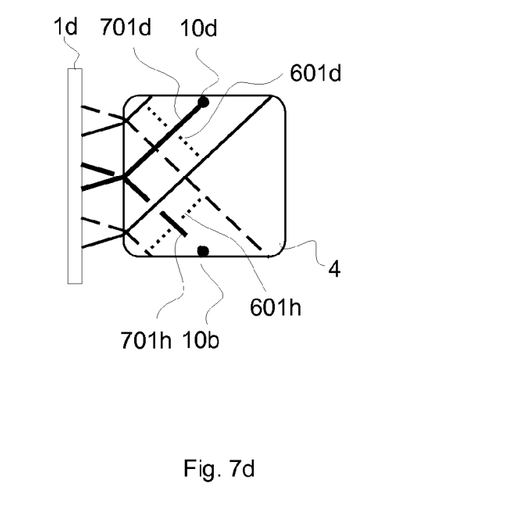
Figure 8A:
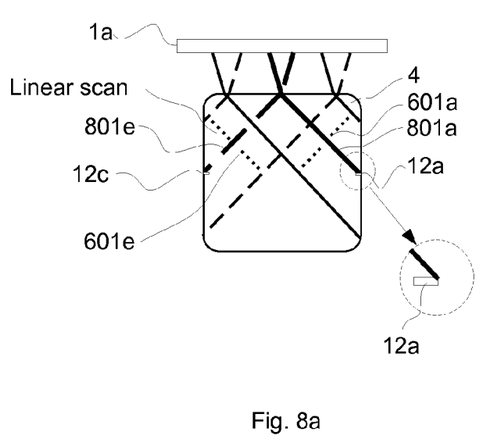
FIGS. 8a, 8b, 8c and 8d describe the overall sensitivity calibration step (step 2) by using four surface standard notches 12a to 12d, each respectively on a side wall.
Figure 8B:
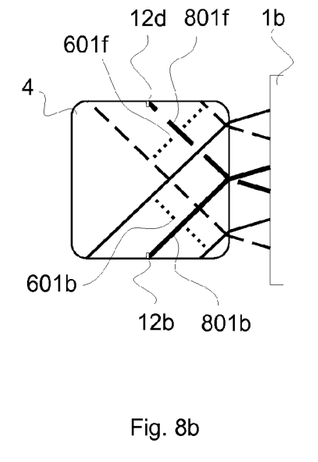
Figure 8C:
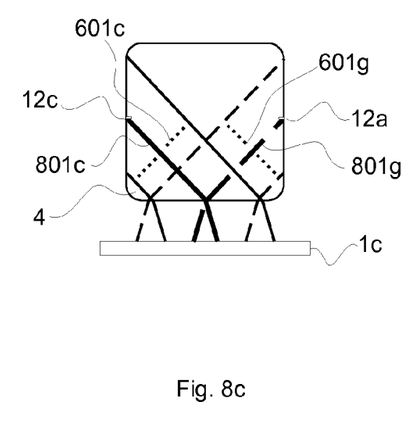
Figure 8D:
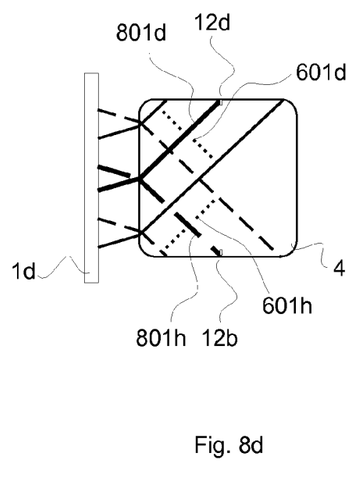

Referring to FIG. 5, an operations process is described in a flow-chart diagram showing the steps of the shear wave beam calibration for square bar inspection according to the present disclosure. To summarize the foregoing description, the process of calibrating a PA probe for shear wave, square bar inspection includes two steps. In step 501, the process of equilibrating all the elements of probe 1 is done by adjusting the gain of each element so that the received amplitude of each element is the same value. In step 502, as detailed in the foregoing description associated with FIGS. 4a and 4b, the probe is further calibrated by using one of the standard reflectors (indicators) in the same way as existing PA sensitivity calibration is performed.

It should be noted that the first step of equilibration (501) is built in many existing PA system, mostly in the form of executable software. Once given a command, the PA system can automatically perform the equilibration by analyzing and adjusting gains of the probe elements. The novel aspect of the present invention is to provide the calibration square bar, with the tilted and equal-depth notches in the manner as presented in this disclosure.

Description of Alternative Embodiments

Reference is now made to FIGS. 6-8. In most of field in-line operations, at least four probes are often used for inspecting respectively four wall surfaces concurrently. Therefore, four probes, 1a, 1b, 1c and 1d are shown to be calibrated using the same process as described above associated with FIGS. 1-5.

It should be noted that the entire description of the basic embodiment associated with FIGS. 1-5 applies to the alternate embodiments and should be construed in a complementary manner. This description of alternative embodiments only focuses on the aspects that are extended from or different from the basic embodiment.

As can be seen in FIGS. 6a, 6b, 6c and 6d, linear scan channels 601a to 601d are used for conducting clock-wise, shear wave linear scan; channels 601e to 601h are used for conducting counter-clock-wise, shear wave linear scan. Calibration bar 4 is machined with four zones of tilted notches, namely 3a, 3b, 3c and 3d, respectively, for equilibration process. Therefore, probe 1a can be equilibrated for both notches in zone 3a and 3c by using channels 601a and 601e, respectively. It should also be noted that notches 3a can be inspected, and can be used for equalization of both probes 1a and 1c by using channels 601a and 601g, respectively.

The equilibration process for each one of the any four probes on each one of the any four zones of notches is the same as in step 501 shown in FIG. 5, and described in the foregoing description associated with FIGS. 1 and 2.

Referring now to FIGS. 7a, 7b, 7c and 7d, sensitivity calibration steps (step 2) can be done by using standard near wall SDHs 10a, 10b, 10c and 10d, in the same way as it's shown in descriptions associated with FIGS. 4a, 4b and 5.

It can be noted that each linear scan channel, such as 601a has a beam 701a "beam corresponding to the SDH", similar to that of in FIGS. 4a and 4b as explained in previous paragraph [0033].

FIG. 7 describes the overall sensitivity calibration of step 2 by using 4 subsurface SDHs 10a to 10d that are parallel to the bar axis. One SDH, such as 6a in the mid-depth of a surface can be used to calibrate the overall sensitivities of both a clock-wise channel 601a and a counter-clock-wise channel 601g, respectively from two PA probes, 1a and 1c. Note that here the 8 channels are assumed to be equilibrated at different sensitivities in the above equilibration process (step 1) associated with FIGS. 6a-6d. During the overall sensitivity calibration (step 2), the sensitivity of the beam corresponding to a SDH is measured and the sensitivities of the beams detecting the same surface are compensated equally.

Similarly, FIGS. 8a-8d describe the overall sensitivity calibration (step 2) by using 4 surface standard notches 12a to 12d with their longitudinal direction parallel to the bar axis. Because one standard notch, such as 12a in the mid-depth of a surface can be used to calibrate the overall sensitivities of both a counter-clockwise channel 601a and a clockwise channel 601g, respectively from two PA probes, 1c and 1a, to calibrate the overall sensitivities of 1c and 1a. It should be noted that it is herein assumed that 601a~601h channels are equilibrated at the previous equilibration the step 1 associated with FIGS. 6a~6b. It should be appreciated by those skilled in the art that, during the overall sensitivity calibration, the sensitivity of the beam corresponding to a notch, such as beam 801a is calibrated and the sensitivities of all the beams detecting the same surface are automatically compensated.

Although the present invention has been described in relation to particular embodiments thereof, many other variations and modifications and other uses will become apparent to those skilled in the art. For example, such variation might include but not limited to using the presently disclosed method to produce test target and scan images of inspection signals generated by all types of NDT/NDI instruments. It is preferred, therefore, that the present invention not be limited by the specific disclosure herein, but only by the appended claims.

What is claimed is:

1. A phased array non-destructive inspection system configured to perform shear wave inspection on a target square bar, the system comprising:
    at least one phased probe having a plurality of apertures, with each aperture having at least one ultrasonic inspection element and the probe is applied with ultrasonic focal laws to form a linear scan channel which includes a plurality of ultrasonic beams, with each of the beams having echo signals including an echo amplitude, and each of the beams corresponds to one of the apertures;
    a longitudinal calibration square bar having four side walls as four test surfaces, at least one test surface thereof having an array of parallel linear notches indented across substantially a full range of the test surface, a longitudinal direction of the linear notches having a direction largely in a same direction as an axial direction of the calibration square bar, the calibration square bar configured to be passed through the probe with the axial direction of the calibration square bar perpendicular to an active direction of the probe during the inspection,
        wherein each inspection beam passes across at least one of the notches, and the inspection system is configured to conduct an equilibration of the probe by adjusting each inspection element so that the echo amplitude for each beam corresponding to each said notches is presented as substantially equal,
        wherein the notches are tilted such that the longitudinal direction of the notches and the axial direction of the calibration square bar form a tilted angle $\alpha$, the relationship among notch pitch d, notch length L and the tilted angle $\alpha$ is defined as:

$d < L \sin \alpha$.

2. The inspection system of claim 1, wherein the calibration square bar has substantially the same size and shape as that of the target square bar.

3. The inspection system of claim 2, wherein the titled angle $\alpha$ is in a range of 3 to 5 degrees.

4. The inspection system of claim 1, further comprising a software or firmware module which can be executed to perform the equilibration of the probe by automatically adjusting the gain of each element so that the echo amplitude for each beam corresponding to each notch is presented as substantially equal.

5. The inspection system of claim 1, wherein the calibration square bar is further configured with a known standard reflector on or near the at least one test surface, the known standard reflector having a size and a shape of flaws associated with testing targets of the type of said target square bar,
    wherein a sensitivity of the inspection system is calibrated by adjusting a baseline amplitude received from an echo signal from the reflector to a predetermined operation level.

6. The inspection system of claim 5, wherein the baseline amplitude is obtained from one of the beams having a maximum amplitude echo from a standard reflector.

7. The inspection system of claim 5, wherein the standard reflector is a side-drill-hole machined near the at least one test surface and parallel to the axial direction of the calibration square bar.

8. The inspection system of claim 5, wherein the standard reflector is a standard notch near the at least one test surface and parallel to the axial direction of the calibration square bar.

9. The inspection system of claim 1, wherein the linear scan channel is one of a clock-wise and a counter-clock-wise linear scan channel.

10. The inspection system of claim 1, wherein said test surface with the notches is configured to enable conducting equilibration of two probes, one with a clock-wise, and the other with a counter-clock-wise linear scan channel.

11. The inspection system of claim 5, wherein said standard reflector is configured to enable calibrating sensitivity of two probes, one with a clock-wise, and the other with a counter-clock-wise linear scan channel.

12. The inspection system of claim 1, wherein the at least one probe comprises four probes, and all said test surfaces having the parallel linear notches.

13. A method of conducting calibration of a phased array non-destructive inspection system and a probe, the system is configured to perform shear wave inspection on a test square bar, and the probe having a plurality of apertures, with each aperture having at least one ultrasonic inspection element and the probe is applied with ultrasonic focal laws to form a linear scan channel which includes a plurality of ultrasonic beams, with each of the beams having echo signals including an echo amplitude, and each of the beams corresponds to one of the apertures,
    the method comprising, providing a longitudinal calibration square bar having four side walls as four test surfaces, at least one test surface thereof has an array of parallel linear notches indented across substantially a full range of said at least one test surface, a longitudinal direction of the linear notches is largely in the same direction as an axial direction of the calibration square bar, the calibration square bar configured to be passed through the probe with the axial direction being perpendicular to an active direction of the probe during the inspection, wherein the notches are tilted so that a longitudinal direction of the notches and an axial direction of the calibration square bar form a tilted angle $\alpha$,
    operating the inspection system so that the ultrasonic beams pass across at least one of the notches, and conducting an equilibration of the probe by adjusting said at least one inspection element so that an echo amplitude for each beam corresponding to each notch is presented as substantially equal, wherein, the relationship among notch pitch d, notch length L and the tilted angle $\alpha$ is defined as:

$d < L \sin \alpha$.

14. The method of claim 13, wherein the calibration square bar has substantially the same size and shape as non-calibration test square bars of a type of said test square bar.

15. The method of claim 13, wherein the titled angle $\alpha$ is in a range of 3 to 5 degrees.

16. The method of claim 13, further comprising the steps of,
providing the calibration square bar with a known standard reflector on or near the at least one test surface, the known reflector having a size and a shape associated with flaws expected from said test bar; and
calibrating a sensitivity of the inspection system by adjusting a baseline amplitude received from an echo signal from the reflector to a predetermined operation level.

* * * * *